United States Patent
Springob et al.

(10) Patent No.: US 11,957,774 B2
(45) Date of Patent: Apr. 16, 2024

(54) COMPOSITION FOR ENHANCING KERATIN FIBERS

(71) Applicant: Wella Germany Gmbh, Darmstadt (DE)

(72) Inventors: Christian Springob, Darmstadt (DE); Ingo Riemann, Darmstadt (DE)

(73) Assignee: Wella Germany Gmbh, Darmstadt (DE)

(*) Notice: Subject to any disclaimer, the term of this patent is extended or adjusted under 35 U.S.C. 154(b) by 0 days.

(21) Appl. No.: 17/704,431

(22) Filed: Mar. 25, 2022

(65) Prior Publication Data
US 2023/0301887 A1    Sep. 28, 2023

(51) Int. Cl.
| | |
|---|---|
| *A61K 8/36* | (2006.01) |
| *A61K 8/31* | (2006.01) |
| *A61K 8/362* | (2006.01) |
| *A61K 8/37* | (2006.01) |
| *A61K 8/891* | (2006.01) |
| *A61Q 5/08* | (2006.01) |
| *A61Q 5/10* | (2006.01) |
| *A61Q 5/12* | (2006.01) |

(52) U.S. Cl.
CPC ............... *A61K 8/362* (2013.01); *A61K 8/31* (2013.01); *A61K 8/361* (2013.01); *A61K 8/37* (2013.01); *A61K 8/375* (2013.01); *A61K 8/891* (2013.01); *A61Q 5/08* (2013.01); *A61Q 5/10* (2013.01); *A61Q 5/12* (2013.01); *A61K 2800/43* (2013.01)

(58) Field of Classification Search
None
See application file for complete search history.

(56) References Cited

U.S. PATENT DOCUMENTS

| | | | |
|---|---|---|---|
| 10,632,054 B2 | 4/2020 | Punyani et al. | |
| 2005/0180941 A1* | 8/2005 | Doi | C11D 1/44 424/70.27 |
| 2006/0223728 A1* | 10/2006 | Tokunaga | A61K 8/463 510/124 |
| 2007/0190009 A1* | 8/2007 | Guentert | A61Q 5/00 424/70.6 |
| 2009/0181059 A1* | 7/2009 | Sakai | A61Q 5/02 424/401 |
| 2020/0206111 A1* | 7/2020 | Lee | A61Q 5/12 |
| 2021/0145716 A9 | 5/2021 | Punyani et al. | |

FOREIGN PATENT DOCUMENTS

| | | |
|---|---|---|
| EP | 3233204 A2 | 10/2017 |
| EP | 3407859 B1 | 12/2018 |
| EP | 3226974 A1 | 6/2021 |

OTHER PUBLICATIONS

Sanusi Umar "Glyceryl Oleate for Hair as a Natural Conditioner, Surfactant and More" <https://ugro.com/glyceryl-oleate-for-hair-as-a-natural-conditioner-surfactant-and-more/> (Year: 2020).*
INCI Beauty <https://incibeauty.com/en/ingredients/> (Year: 2023).*
McDonald, T; Drescher, K.M.; Weber, A.; Tracy, S; "Creatinine inhibits bacterial replication" The Journal of Antibiotics 65, 153-156 (Year: 2012).*

* cited by examiner

*Primary Examiner* — Nicole P Babson
(74) *Attorney, Agent, or Firm* — Dennemeyer & Associates LLC; Victoria Friedman

(57) ABSTRACT

The present invention is directed to a hair treatment composition and method for its use. Embodiments of the hair treatment composition include at least organic acid components comprising an organic dicarboxylic acid and an organic fatty acid, a fatty hydrocarbon and a fatty acid ester. The hair treatment composition can serve as a hair conditioner, a leave-on composition or a shampoo depending upon additional appropriate additives.

21 Claims, No Drawings

COMPOSITION FOR ENHANCING KERATIN FIBERS

FIELD OF THE INVENTION

The present invention relates to a hair treatment composition comprising components providing rehabilitation of damaged keratin fibers, and a method for application of the composition.

BACKGROUND OF THE INVENTION

Keratin fibers and human hair in particular are damaged by daily routines such as brushing and combing, external influences like sun light and pollution and oxidative and/or reductive treatments like hair coloration, bleaching or perming. The damage caused by these activities includes removal of the F-layer fatty acids, breakage of disulfide links of keratin protein and erosion of the keratin protein materials at the surfaces of the hair fiber cuticles. The damage tends to roughen the hair fiber surfaces much like a rasp roughens wood. The roughened hair strands lack smoothness, tend to misbehave and are unruly. Hair care goals have involved attempts to reverse these tendencies.

One such attempt has involved hair care and repair agents such as hair cortex repair formulations and associated methods. It is thought that damage to the hair cortex can result in unravelling cortex protein bundles and can lead to the unruliness and roughness. One possible answer has involved use of crosslinking of dimaleate type of molecules to re-bond cleaved disulfide links in hair cortex. See International Patent Application WO 2015/017768 A1. Another possible answer has involved a method for restructuring of hair fiber cortex with cysteine and at least one dicarboxylic acid. See WO 2005/115314 A1.

However, these methods have been only partially successful. They do not address cuticle erosion, subsurface and surface degradation of keratin protein. Therefore, there is still a need to provide compositions delivering superior hair cuticle repair as this remains one of the key hair concerns of consumers. A further need is the improvement of the integrity and the healthiness of hair and deliver shine, suppleness, a smooth hair feel and good disentangling properties.

SUMMARY OF THE INVENTION

The present invention is directed a hair treatment composition and corresponding method for treatment of the cuticle of keratin fibers, specifically cuticles of anagenic human hair damaged by daily routine and chemical treatment. Embodiments of the hair treatment composition deliver components to protect and repair the damaged cuticles of keratin fibers, such as anagenic hair strands of humans. The compositional components enable repair of broken keratin protein inner connections, smoothing of hair strand roughness, lubrication of hair strands and melding of split strand ends. The compositional components deliver hair strand treatment without causing heavy weighting of hair strands, oiliness, and avoid use of animal and fish components. The compositional components deliver "green technology" to the treatment and conditioning of anagenic hair.

Compositional aspects of the invention are directed to embodiments of a primary hair treatment composition involving at least three and preferably four organic components. The hair treatment composition may comprise a stand-alone hair conditioner formulation such as a rinse-off or leave on conditioner or may comprise a conditioning feature of a sulfate shampoo or sulfate-free shampoo. The components of the hair treatment composition are green-oriented in that they may be derived from plant material and/or may be synthetic and/or semi-synthetic derivatives thereof.

The hair treatment composition may comprise at least the four component combination of a C3-C13 linear or branched, saturated or unsaturated dicarboxylic acid wherein the saturated dicarboxylic acid optionally may include one hydroxyl, a C10-C30 linear or branched, saturated or unsaturated fatty monocarboxylic acid, C10-C40 linear or branched saturated or unsaturated hydrocarbon and a fatty acid ester of the C10-C30 linear or branched saturated or unsaturated fatty monocarboxylic acid and a C3-C6 mono-ol, diol or triol. Each acid of this composition may independently and individually be in the form of the free carboxylic acid or cosmetically acceptably salt thereof. The hair treatment composition also comprises a cosmetically acceptable aqueous or aqueous-organic medium.

Additional components for incorporation into the hair treatment composition include one or more saturated or unsaturated fatty C20-C30 alcohols; one or more cationic surfactants such as but not limited to quaternary ammonium compounds formed of one or more saturated and/or unsaturated fatty C20-C30 amines quaternized with one to three C1-C3 alkyl groups. Further additives include liquid silicones, anti-oxidants, preservatives, anti-oxidants, anti-microbials, UV protectants, fragrance, viscosity control agents, surfactants, humectants, emollients, hair strand thickeners for providing strand body such as but not limited to silicas, diatomaceous earth, clays such as kaolin and smectite phyllosilicates and color and/or shine agents.

Use embodiments of the hair treatment composition according to the invention comprise a sulfate shampoo, a non-sulfate shampoo, a non-ionic surfactant hair cleaning liquid, a stand-alone conditioner, a mask, a leave on treatment, a rinse off conditioner, a hair rinse, a hair liquid, a hair oil, a hair pomade, a hair foam, a hair spray, a hair tonic and/or hair lotion, all with the hair treatment composition as at least a part of the use embodiment.

A further embodiment of the invention comprises a method for applying the hair treatment composition and/or any of its use embodiments to hair, preferably anagenic hair.

DEFINITIONS

Unless defined otherwise, all technical and scientific terms used herein have the same meaning as commonly understood by a person of ordinary skill in the art.

As used in the specification and the appended statements, the singular forms "a," "an" and "the" include plural referents unless the context clearly dictates otherwise.

The term "may" in the context of this application means "is permitted to" or "is able to" and is a synonym for the term "can." The term "may" as used herein does not mean possibility or chance.

The term and/or in the context of this application means one or the other or both. For example, an aqueous solution of A and/or B means an aqueous solution of A alone, an aqueous solution of B alone and an aqueous solution of a combination of A and B.

The term "about" is understood to mean±10 percent of the recited number, numbers or range of numbers.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4. Similarly, values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

The term "anagenic hair" as used herein means hair strands that are in direct connection with a hair follicle which is in either the anagen or telogen state. Anagenic hair is present in one of these states on a scalp of a person, a human, and its follicle is appurtenant to a sebum gland that substantially continuously secretes sebum and long chain fatty acids onto the surfaces of the hair shaft. As the hair grows from the follicle, it carries with it coatings of secreted sebum and long chain fatty acids. The fatty acid coating is known as the f layer and is tightly entwined with the keratin protein at the hair shaft surface. Hair cut from a living person is no longer anagenic hair.

Keratin fibers means hair strands on the scalp of a person, preferably anagenic hair. Keratin fibers, aka hair strands, are comprised of cells forming an inner cortex as the core and a cuticle as the outer covering surrounding the cuticle. The hair strand chemical components include proteins, polynucleic acids, amino acids, minerals, melanin, lipids including fatty acids, fatty alcohols, triglycerides, phospholipids, cholesterol, and squalene. These components are configured as cells, fibrils, connective tissue, extracellular links, pigments, keratin and associated structures. The outer layer of the cuticle is configured as a sheath of overlapping flat cells having a structure like the bark of a palm tree or scales of a fish. Like the scales of a fish, the surface of the cuticle is smooth in the direction from the root to the tip and rough in the direction from the tip to the root.

DETAILED DESCRIPTION

The present invention is directed to a hair treatment composition that delivers components and substances for replenishment of, and addition to, damaged anagenic hair. The hair treatment composition may be incorporated as a facet of another cosmetic composition such as a shampoo or may formulated as a stand-alone composition such as but not limited to a conditioner composition.

Anagenic hair can be damaged by wear and degradation caused by perming, redox treatment, shampooing, brushing, combing and/or rubbing such as with towels, hats, caps and the like. These activities performed on anagenic hair strands cause the strands to be thinned, broken, fragmented, splintered and otherwise damaged. This damage is believed to result from lift of the cellular scales on the surfaces of the cuticles of the hair strands and removal of lubricating substances from the scales. The lift and de-lubrication enable breakage, dislodgement, fragmentation and disruption of the inter-scale connections of fatty acids, phospholipids and disulfide bonds. Water, soap, shampoo and similar solubilization agents are able to permeate the cuticle as a result of the lifted individual scales of the cuticle. This permeation enables dilution, solubilization and dispersion of the micro connections between the lifted scales. The result is a weakening of the hair strand cuticle leading to breakage, fragmentation and splintering of the strand.

Embodiments of the hair treatment composition according to the invention replace and reincorporate the inter-scale connections of hair strands, coat hair strand scale surfaces and close inter-scale spaces resulting from lift. The result is believed to strengthen the hair strands and render them less susceptible to lift. The strengthening can be measured by the ease of combability of such treated hair strands.

The hair treatment composition comprises a cosmetically acceptable aqueous or aqueous-organic medium and at least four components comprising the above described C3-C13 dicarboxylic acid, the above described C10-C30 fatty monocarboxylic acid, the above described C10-C40 hydrocarbon and the above described C10-C30 fatty acid ester. These four components are present at weight percentage ranges relative to the total weight of the composition of:

a) about 0.05 wt % to about 15 wt %, preferably about 0.1 wt % to about 10 wt % for the dicarboxylic acid;
b) about 0.01 wt % to about 10 wt %, preferably about 0.015 w % to about 1 wt % for the fatty acid;
c) about 0.01 wt % to about 1.0 wt % for the hydrocarbon; and
d) about 0.01 wt % to about 10 wt %, preferably about 0.1 wt % to about 9 wt % for the fatty acid ester.

The concentration ranges of the dicarboxylic acid and the fatty monocarboxylic acid follow a general relationship in which the weight percentage relative to the total weight of the composition is larger for the dicarboxylic acid than for the fatty monocarboxylic acid. The ratio of dicarboxylic acid to fatty monocarboxylic acid ranges from about 2:1 to about 10:1, preferably about 2:1 to about 5:1. The weight percentage sum of the lipid components including at least the hydrocarbon and the fatty acid ester may be present in the hair treatment composition at concentrations ranging from about 0.01% to about 10.0 wt % relative to the total weight of the entire composition. The hydrocarbon part of this component may range from about 0.01 to about 0.1 wt % and the remainder of the lipid component may be the fatty ester. The weight percentage ratio of the sum of the dicarboxylic acid and fatty monocarboxylic acid components to the sum of the lipid components comprising the hydrocarbon and the fatty acid ester may range from about 10:1 to about 1:1, preferably about 5:1 to about 1.5:1, more preferably about 4:1 to about 2:1.

Preferred embodiments of the dicarboxylic acid, the fatty monocarboxylic acid, the fatty hydrocarbon and the fatty acid ester include at least a linear or branched saturated C3-C6 dicarboxylic acid optionally with one hydroxyl, a linear unsaturated C4-C6 dicarboxylic acid, a branched unsaturated C5-C6 dicarboxylic acid with the branch being an olefinic group, more preferably a linear saturated C3-C6 dicarboxylic acid with one hydroxyl; at least a C14-C22 linear saturated or unsaturated fatty monocarboxylic acid, more preferably a C16-C18 linear unsaturated fatty monocarboxylic acid; at least a C26-C30 saturated or unsaturated linear or branched fatty hydrocarbon or similar hydrocarbon, more preferably a C28-C30 branched saturated or unsaturated fatty hydrocarbon; and at least a C14-C22 linear saturated or unsaturated fatty monocarboxylic acid ester esterified with a C3-C6 mono-ol, diol or triol, preferably C16-C18 linear unsaturated fatty carboxylic acid ester esterified with a C3 triol.

Preferred named embodiments of the C3-C13 dicarboxylic acid include malonic acid, succinic acid, glutaric acid, adipic acid, brassylic acid, malic acid, 2-methyl malic acid, hydroxysuccinic acid, 2-hydroxy-3-methylsuccinic acid, hydroxyglutaric acid, 2-hydroxy-3-methylglutaric acid, hydroxyadipic acid, fumaric acid, maleic acid, itaconic acid, and glutaconic acid. An especially most preferred embodiment of the dicarboxylic acid comprises malic acid.

Preferred named embodiments of the fatty C14-C22 saturated and unsaturated, linear fatty mono carboxylic acid comprise myristic acid, palmitic acid, stearic acid, arachidic acid, behenic acid, palmitoleic acid, sapienic acid, oleic acid, elaidic acid, vaccenic acid and linoleic acid. More preferred fatty acids include the C16-C18 saturated and unsaturated fatty acids. Especially more preferred fatty acids include the unsaturated fatty acids palmitoleic and oleic acids with oleic acid being the most especially preferred example.

Each of the dicarboxylic acid and the fatty monocarboxylic acid components of the hair treatment composition may independently be in the free carboxylic acid form or may be a cosmetically acceptable salt thereof in which the gegenion may be the alkali or alkaline earth metal cations that do not cause precipitation of the salt form, preferably including the sodium, potassium, lithium, magnesium, zinc, copper and aluminum cations, more preferably sodium, potassium and lithium, especially more preferably sodium and potassium.

The lipid components at least comprise the C10-C40 hydrocarbon and the C14-C22 fatty acid ester and may comprise other hydrocarbons as well as other lipids. Exemplary hydrocarbons include a C26-C40 hydrocarbon, preferably a C28-C30 hydrocarbon, Named exemplary hydrocarbons include liquid petroleum, squalane, squalene, tri and tetra terpenes, iso-paraffin and mineral oil. A preferred hydrocarbon is squalane or squalene with squalane being more preferred. The fatty acid ester preferably comprises the above identified preferred C16-C18 linear saturated or unsaturated fatty monocarboxylic acid which is esterified with a C3-C6 mono-ol (a monoalcohol), a diol or a triol, preferably a triol, more preferably a C3 or C4 trio. and most preferably glycerin. A preferred fatty acid ester is glyceryl mono-palmitoleate, glyceryl monooleate or a combination thereof with glyceryl monooleate alone being more preferred.

Preferably, when the hair treatment composition comprises a component of a sulfate and/or a sulfate-free shampoo, the lipid component may optionally comprise two versions of the fatty acid ester including the mono fatty acid ester formed with a triol and a di fatty acid ester formed with a triol. When the hair treatment composition comprises a component of a sulfate free shampoo, the lipid component may optionally include the hydrocarbon as a substitute for the di fatty acid ester of the mono and di fatty acid ester combination. When the hair treatment composition comprises a stand-alone conditioner, a mask, a leave on treatment, a rinse off conditioner, a hair rinse, a hair liquid, a hair oil, a hair pomade, a hair foam, a hair spray, a hair tonic and/or hair lotion, the lipid component may be both of a mono fatty acid ester formed with a triol and a hydrocarbon.

pH of the Composition

Embodiments of the present invention incorporate not only the organic acid component but also organic acidifying and basifying agents such as citric acid, acetic acid, tartaric acid, hydrochloric acid and alkali metal hydroxides such as sodium or potassium hydroxide. These agents enable balance of the pH of a composition of the present invention so that it is not an irritant to humans such as human scalp and/or face. Consequently, the acidifying and basifying agents may be adjusted so that the pH is in the range of about 5 to about 9, preferably in a range of about 6 to about 8.

Additional Components

Additional components for embodiments of the hair treatment composition depend at least in part upon the purpose and function of the hair treatment composition. For example, if the hair treatment composition is to be a part of a shampoo, anionic and/or nonionic surfactants may be included. If the hair treatment composition is to be a part of a rinse off or leave on conditioner, cationic surfactants and/or cationic polymers may be included. Moisturizers, humectants, thickeners, emulsifiers as well as other additives for delivering advantageous qualities may be included the hair treatment composition.

Conditioner Composition

The hair treatment composition of the present invention may comprise a cationic surfactant, an optional silicone component and aqueous carrier. The surfactants, silicones and the aqueous carrier may be in the form of emulsion.

Cationic Surfactant System

The composition of the present invention may optionally comprise a cationic surfactant system especially when the composition of the present invention is to deliver conditioning properties. The cationic surfactant system may comprise one cationic surfactant or a mixture of two or more cationic surfactants. When present, the cationic surfactant system may be included in the composition at a level by weight of from about 0.1% to about 10%, preferably from about 0.5% to about 8%, more preferably from about 0.8% to about 5%, still more preferably from about 1.0% to about 4% relative to the total weight of the composition. Embodiments of cationic surfactants useful in the hair treatment composition of the invention include common and ordinary quaternary ammonium salts of C14-C30 linear alkyl amines quaternized with three methyl groups. Examples include behentrimonium chloride, stearyl trimonium chloride and similar trimonium compounds.

Silicone Conditioning Agent

The hair treatment composition of the present invention may also comprise one or more silicone conditioning agents. Examples of the silicones include dimethicones, dimethiconols, cyclic silicones, and modified silicones with various functional groups such as amino groups, quaternary ammonium salt groups, and amine silicones such as Amodimethicone. Such silicones may be soluble or insoluble in the aqueous (or aqueous-organic) medium. In the case of insoluble liquid silicones, the polymer can be in an emulsified form with droplet size of about 10 nm to about 30 micrometers. Other solid or semi-solid conditioning agents may be present in the composition including high melting temperature fatty alcohols, acids, esters, amides or oligomers from unsaturated esters, alcohols, amides. The oligomeric esters may be the result of oligomerization of naturally-occurring unsaturated glyceride esters. Such solid or semi-solid conditioning agents may be added or present as mixtures with organic oils.

Shampoo Surfactant

When embodiments of the hair treatment composition are formulated as a shampoo, the shampoo will include a surfactant such as a sulfate or non-sulfate anionic surfactant or a non-ionic surfactant or any combination thereof. According to the invention, embodiments of surfactant component of the shampoo composition may comprise at least one member of the anionic surfactant class including a sulfate anionic surfactant or a non-sulfate anionic surfactant. The anionic surfactant class may also include multiple species of each member as well as a combination of these class members and any combination of multiple species of both members.

Additionally, the surfactant component may further comprise a non-ionic surfactant in combination with any variation of the anionic surfactant class described above. Preferably, the surfactant component may comprise one or more sulfate anionic surfactants alone, one or more non-sulfate anionic surfactants alone, a mixture of a minor amount of one or more sulfate anionic surfactants and a major amount of one or more non-sulfate anionic surfactants, a mixture of one or more sulfate anionic surfactants and one or more non-ionic surfactants, or a mixture of one or more non-sulfate anionic surfactants and one or more non-ionic surfactants. More preferably, the surfactant component may comprise one or more non-sulfate anionic surfactants alone. Also preferably, the surfactant component may comprise one or more non-sulfate anionic surfactants combined with one or more non-ionic surfactants. Especially more preferably the surfactant component may comprise a combination of two members of the surfactant class such as but not limited to a combination of one or more sulfate-free non-sulfate anionic surfactants and one or more non-ionic surfactants.

Another especially preferred surfactant class may comprise any of the embodiments including a non-sulfate anionic surfactant which may be devoid of any sulfate anionic surfactant. This surfactant class may be characterized as a sulfate-free non-sulfate anionic surfactant. Without the characterization of "sulfate free", a surfactant component comprising a non-sulfate anionic surfactant and/or a non-ionic surfactant may include but not necessarily include a minor concentration to an almost indetectable concentration of sulfate anionic surfactant which may be incidentally or purposefully present.

The sulfate anionic surfactant class of the surfactant component of the present shampoo composition may comprise a branched and/or linear C8 to C20 alkyl sulfate, a linear and/or branched C8 to C20 alkyl benzene sulfate or a linear and/or branched C8 to C20 alkyl benzyl sulfate or the corresponding ether and/or glyceryl and/or sugar alcohol derivatives obtained from ethylene epoxide/ethylene glycol, propylene epoxide/1,2-propylene glycol, glycerin and/or sugar alcohol monomers. The linear and/or branched alkyl group may be a single chain length or may be a mixture of chain lengths.

Exemplary sulfate anionic surfactants comprise one or more of sodium lauryl sulfate, sodium laureth sulfate, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric mono glyceride sodium sulfate, sodium lauryl sulfate, sodium laureth sulfate, potassium lauryl sulfate, potassium laureth sulfate, ammonium cocoyl sulfate, sodium cocoyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfate, sodium dodecyl benzene sulfate.

The non-sulfate anionic surfactant class of the surfactant component of the present shampoo composition may be selected from the group of acyl isethionates/methyl isethionates, acyl glycinates, acyl taurates, acyl amino acids, acyl sarcosinates, sulfosuccinates and sulfonates, wherein the acyl groups of all these surfactant classes comprise from 6 to 30 carbon atoms. The non-sulfate anionic surfactant may also comprise more than one of these surfactants and may comprise mixtures thereof. The non-sulfate anionic surfactant segment may also comprise the alkaline and alkaline earth salts of one or more or mixtures of individual compounds of any of these surfactant classes and mixtures thereof.

Fatty Alcohols

Fatty alcohols may optionally be included in embodiments of the shampoo and conditioning hair treatment compositions of the invention. The fatty alcohols provide emulsifying, occlusive, moisturizing, thickening and humectant properties to the hair treatment composition. Included are fatty alcohols and mixtures thereof having a linear or branched carbon chain of from about 12 to about 30 carbons, The fatty alcohols may be saturated or unsaturated. Preferred fatty alcohols include lauryl alcohol, myristyl alcohol, cetyl alcohol, stearyl alcohol, behenyl alcohol, oleyl alcohol, arachidyl alcohol and mixtures thereof such as cetearyl alcohol (mixture of cetyl and stearyl alcohols).

Medium

The hair treatment composition of the present invention may comprise an aqueous carrier as cosmetically acceptable medium. Accordingly, embodiments of the compositions of the present invention can be in the form of pourable liquids (under ambient conditions). Such compositions will therefore typically comprise an aqueous carrier, which may be present at a level of from about 20 wt. % to about 95 wt. %, or from about 60 wt. % to about 85-90 wt. %. The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier useful in the present invention may alternatively comprise water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol. Aqueous-organic carriers for the hair treatment compositions of the invention may comprise from about 50 wt % to about 99 wt % water, preferably about 75 wt % to about 95 wt % water, more preferably about 85 wt % to about 95 wt % water with the remainder being a mono or polyhydric alcohol, preferably any one or a mixture of any two or more of ethanol, isopropanol, propylene glycol and glycerin.

Further Optional Ingredients

The compositions of the present invention can also additionally comprise any other suitable optional ingredients as desired. For example, the composition can optionally include other active or inactive ingredients known for scalp health benefits.

In an embodiment of the present invention, a scalp health active may be added to provide scalp benefits. This group of scalp health materials is varied and provides a wide range of benefits including anti-dandruff, anti-fungal, anti-microbial, moisturization, barrier improvement, and anti-oxidant, anti-itch, and sensates. Such health actives include but are not limited to: zinc pyrithione, climbazole, octopirox, vitamin E and F, salicylic acid, phenoxyethanol, ethylhexyl glycerin, glycols, glycolic acid, PCA, PEGs, erythritol, glycerin, lactates, hyaluronates, allantoin and other ureas, betaines, sorbitol, glutamates, xylitols, menthol, menthyl lactate, isocyclomone, benzyl alcohol, and natural extracts/oils including peppermint, spearmint, argan, jojoba and aloe. The compositions may include other common hair ingredients. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein. Examples of these ingredient classes include but are not limited to: aesthetic components such as fragrances, pigments, colorings/colorants, essential oils, sensates, antifoaming agents, antimicrobial agents, biological additives, buffering agents, bulking agents, chelating agents, chemical additives, astringents, biocides, film formers or materials, pH adjusters, reducing agents, sequestrants, and surfactants.

Method of Application

The hair treatment composition may be applied neat to anagenic hair (hair on the head of a human) or may be diluted with water or a combination of water and a water miscible alcohol and applied to anagenic hair. After application, the hair treatment composition on the hair may be massaged and worked through the hair to distribute the composition throughout the hair. The Following a sufficient time to accomplish cleaning, conditioning, and/or other function of the hair treatment composition on the hair, the hair may be rinsed with water or if the hair treatment composition is a leave on, the hair may be troweled briefly to remove excess composition if any.

EXAMPLES

The following examples illustrate the present invention. The exemplified compositions can be prepared by conventional formulation and mixing techniques. It will be appreciated that other modifications of the present invention within the skill of those in the hair care formulation art can be undertaken without departing from the spirit and scope of this invention. All parts, percentages, and ratios herein are by weight unless otherwise specified. Some components may come from suppliers as dilute solutions.

It has been surprisingly discovered that a hair conditioning composition containing a combination of at least the dicarboxylic acid, the fatty monocarboxylic acid, the fatty hydrocarbon and the fatty acid ester improves the combability of damaged hair and improves the quality of the hair cuticle.

Combing Force Measurement

Various external influences, such as certain cosmetic treatments (bleaching, coloring, permanent waving), exposure to the weather, frequent combing and brushing affect the combing ease due to a degradation of the hair cuticle. Thus, the combing ease of hair is a major parameter for describing the quality/degree of damage of hair on the one hand and/or the effectiveness of conditioning respectively hair repair treatments on the other hand.

The principle of most methods for the determination of combing properties consists in measuring the force to pull a comb through a hair tress under definite conditions (Ref.: C. R. Robbins, Chemical and Physical Behavior of Human Hair, 5th Edition, p. 646 ff., Springer-Verlag, Berlin Heidelberg 2012. ISBN 978-3-642-25610-3).

For this test, an automated device is used in which the tresses to be tested are taken from a storage chamber and are fixed to a force meter. The tresses are combed automatically at constant speed. For each combing stroke the combing force is recorded as a function of the distance combed through (length of the tress). For comparison purposes 20 combing strokes per tress on at least 3 tresses per product sample are averaged.

The Wet Combing Force is the average force along the tress. The lower the combing force the better the combing ease.

Hair Tresses Preparation for the Combing Force Measurements

Hair tresses (Caucasian hair), weight 2 g, 17 cm long, medium-blonde color, are two times bleached to simulate hair damage and then soaked in city water for 10 min (35° C.±2° C.). Afterwards, the tresses are adjusted to 50% rel. humidity by weight, then combed twice (rough & fine side of comb). 0.25 ml/g hair of the hair care composition to be tested are applied to the tresses and massaged in for 1 min. The tresses are rinsed off for 1 min using city water (6 L/min; 35° C.±2° C.). Afterwards, the tresses are adjusted to 50% rel. humidity by weight. The tresses are combed twice (rough & fine side of comb) and placed inside a wet magazine of the combing device storage chamber for the actual wet combing force measurements.

Examination Results

The following table shows the measured wet combing forces in Newton (N) of hair swatches subjected to damage and then treated with the hair treatment composition according to the invention as well as treatment compositions lacking one or more of the four components of the hair treatment composition of the invention. The treated hair swatches subjected to the mechanical combing measurement described above include:

a) virgin hair,
b) damaged hair (two times bleached),
c) damaged hair (two times bleached) treated with a liquid composition of example 6 including the four components of the hair treatment composition: dicarboxylic acid, fatty acid, fatty acid ester, hydrocarbon),
d) damaged hair (two times bleached) treated with a liquid composition containing the ingredients of example 6 including the dicarboxylic acid except that this composition does not contain the lipids or fatty acid of example 6; this is example 8;
e) damaged hair (two times bleached) treated with a liquid composition containing the ingredients of example 6 including the lipids and fatty acid except that this composition does not contain the dicarboxylic acid of example 6; this is example 9;
f) damaged hair (two times bleached) treated with a liquid composition containing the ingredients of example 6 except that this composition does not contain the lipids, fatty acid and dicarboxylic acid of example 6; this is example 10.

| Combing Force/N | Sample |
|---|---|
| 0.125 | a) Untreated (virgin hair) |
| 0.293 | b) 2× bleached (damaged hair) |
| 0.073 | c) 2× bleached + treated with example 6 (composition with lipids, fatty acid and dicarboxylic acid) |
| 0.091 | d) 2× bleached + treated with example 8 (composition without lipids or fatty acid but with dicarboxylic acid) |
| 0.093 | e) 2× bleached + treated with example 9 (composition with lipids and fatty acid but without dicarboxylic acid) |
| 0.087 | f) 2× bleached + treated with example 10 (composition without lipids, without fatty acid and without dicarboxylic acid) |

The results indicate clearly that hair treated with compositions containing lipids plus fatty acid and dicarboxylic acid (sample c, example 6) show better combing (lower combing forces) versus compositions containing only dicarboxylic acid (sample d, example 8) or only lipids and fatty acid but no dicarboxylic acid (sample e, example 9) or no lipid, no fatty acid and no dicarboxylic acid (sample f, example 10).

Thus, the combination of lipids, fatty acid and dicarboxylic acid shows a synergistic effect on combability respectively hair repair effectiveness.

Example 1 (Shampoo)

| Raw Material | Amount |
| --- | --- |
| Sodium Laureth Sulfate, 70% in water | 8.6 g |
| Sodium Lauryl Sulfate, 29% in water | 19.0 g |
| Cocamidopropyl Betaine, 30% in water | 6.7 g |
| Guar Hydroxypropyltrimonium Chloride | 0.3 g |
| Dimethicone 330M | 1.0 g |
| Cocamide MEA 85% | 1.0 g |
| Ethylene Glycol Distearate | 1.5 g |
| Oleic Acid | 0.01 g |
| Glyceryl Monooleate | 0.01 g |
| Citric Acid | 0.4 g |
| Glutaric Acid | 0.1 g |
| Sodium Benzoate | 0.5 g |
| Salicylic Acid | 0.2 g |
| Tetrasodium EDTA | 0.16 g |
| Perfume | 0.7 g |
| Sodium Chloride | 0.15 g |
| Water | to 100 g |

Example 2 (Shampoo)

| Raw Material | Amount |
| --- | --- |
| Sodium Laureth Sulfate, 70% in water | 8.6 g |
| Sodium Lauryl Sulfate, 29% in water | 19.0 g |
| Cocamidopropyl Betaine, 30% in water | 6.7 g |
| Guar Hydroxypropyltrimonium Chloride | 0.2 g |
| Dimethicone 330M | 1.1 g |
| Cocamide MEA 85% | 1.0 g |
| Ethylene Glycol Distearate | 1.5 g |
| Oleic Acid | 0.1 g |
| Glyceryl Monooleate | 0.2 g |
| Malic Acid | 0.5 g |
| Squalane | 0.05 g |
| Sodium Benzoate | 0.5 g |
| Salicylic Acid | 0.2 g |
| Tetrasodium EDTA | 0.16 g |
| D,L-Tocopheryl Acetate | 0.2 g |
| Perfume | 0.7 g |
| Sodium Chloride | 0.15 g |
| Water | to 100 g |

Example 3 (Sulfate-Free Shampoo without Hydrocarbon)

| Raw Material | Amount |
| --- | --- |
| Sodium Methyl Oleoyl Taurate | 2.5 g |
| Sodium Lauroyl Sarcosinate | 1.5 g |
| Cocamidopropyl Betaine | 4.5 g |
| Polyquaternium-10 | 0.4 g |
| Malic Acid | 0.3 g |
| Oleic Acid | 0.05 g |
| Glyceryl Monooleate | 0.1 g |
| Sodium Benzoate | 0.4 g |
| Perfume | 0.5 g |
| Water | to 100 g |

Example 4 (Rinse-Off Conditioner/Mask without Hydrocarbon)

| Raw Material | Amount |
| --- | --- |
| Cetyl Alcohol | 8.0 g |
| Paraffinum Liquidum | 3.0 g |
| Isopropyl Myristate | 3.0 g |
| Cetrimonium Chloride | 1.0 g |
| Behentrimonium Chloride | 0.4 g |
| Amodimethicone | 0.3 g |
| Ceteareth-25 | 1.5 g |
| Coco-Glucoside | 0.45 g |
| Glyceryl Monooleate | 0.45 g |
| Polyquaternium-37 | 0.125 g |
| Oleic Acid | 0.1 g |
| Malic Acid | 3.0 g |
| Sodium Hydroxide | 1.0 g |
| Disodium EDTA | 0.1 g |
| Phenoxyethanol | 0.9 g |
| Ethylhexylglycerin | 0.1 g |
| Perfume | 0.3 g |
| Water | to 100 g |

Example 5 (Rinse-Off Conditioner/Mask)

| Raw Material | Amount |
| --- | --- |
| Cetyl Alcohol | 8.0 g |
| Paraffinum Liquidum | 3.0 g |
| Isopropyl Myristate | 3.0 g |
| Cetrimonium Chloride | 1.0 g |
| Behentrimonium Chloride | 0.4 g |
| Amodimethicone | 0.3 g |
| Ceteareth-25 | 1.5 g |
| Coco-Glucoside | 0.45 g |
| Glyceryl Monooleate | 0.45 g |
| Polyquaternium-37 | 0.125 g |
| Oleic Acid | 0.1 g |
| Malic Acid | 3.0 g |
| Sodium Hydroxide | 1.0 g |
| Disodium EDTA | 0.1 g |
| Squalane | 0.1 g |
| Phenoxyethanol | 0.9 g |
| Ethylhexylglycerin | 0.1 g |
| Perfume | 0.3 g |
| Water | to 100 g |

Example 6 (Leave-on Treatment)

| Raw Material | Amount |
| --- | --- |
| Propylenglycol | 3.0 g |
| Amodimethicone | 1.3 g |
| Quaternium-80 | 1.0 g |
| Cetrimonium Chloride | 1.0 g |

-continued

| Raw Material | Amount |
| --- | --- |
| Behentrimonium Chloride | 1.6 g |
| Amodimethicone | 0.3 g |
| D,L-Tocopheryl Acetate | 0.2 g |
| Glyceryl Monooleate | 0.25 g |
| Polyquaternium-37 | 0.125 g |
| Oleic Acid | 0.1 g |
| Malic Acid | 0.3 g |
| Sodium Hydroxide | 0.1 g |
| Disodium EDTA | 0.1 g |
| Squalane | 0.1 g |
| Phenoxyethanol | 0.1 g |
| Methylparaben | 0.2 g |
| Perfume | 0.3 g |
| Water | to 100 g |

Example 7 (Leave-on Treatment without Fatty Ester)

| Raw Material | Amount |
| --- | --- |
| Propylenglycol | 3.0 g |
| Amodimethicone | 1.3 g |
| Quaternium-80 | 1.0 g |
| Cetrimonium Chloride | 1.0 g |
| Behentrimonium Chloride | 1.6 g |
| Amodimethicone | 0.3 g |
| D,L-Tocopheryl Acetate | 0.2 g |
| Polyquaternium-37 | 0.125 g |
| Oleic Acid | 0.1 g |
| Malic Acid | 0.3 g |
| Sodium Hydroxide | 0.1 g |
| Disodium EDTA | 0.1 g |
| Squalane | 0.1 g |
| Phenoxyethanol | 0.1 g |
| Methylparaben | 0.2 g |
| Perfume | 0.3 g |
| Water | to 100 g |

Example 8 (Leave-on Treatment without Lipids, without Fatty Acid)

| Raw Material | Amount |
| --- | --- |
| Propylenglycol | 3.0 g |
| Amodimethicone | 1.3 g |
| Quaternium-80 | 1.0 g |
| Cetrimonium Chloride | 1.0 g |
| Behentrimonium Chloride | 1.6 g |
| Amodimethicone | 0.3 g |
| D,L-Tocopheryl Acetate | 0.2 g |
| Polyquaternium-37 | 0.125 g |
| Malic Acid | 0.3 g |
| Sodium Hydroxide | 0.1 g |
| Disodium EDTA | 0.1 g |
| Phenoxyethanol | 0.1 g |
| Methylparaben | 0.2 g |
| Perfume | 0.3 g |
| Water | to 100 g |

Example 9 (Leave-on Treatment without Dicarboxylic Acid)

| Raw Material | Amount |
| --- | --- |
| Propylenglycol | 3.0 g |
| Amodimethicone | 1.3 g |
| Quaternium-80 | 1.0 g |
| Cetrimonium Chloride | 1.0 g |
| Behentrimonium Chloride | 1.6 g |
| Amodimethicone | 0.3 g |
| D,L-Tocopheryl Acetate | 0.2 g |
| Glyceryl Monooleate | 0.25 g |
| Polyquaternium-37 | 0.125 g |
| Oleic Acid | 0.1 g |
| Sodium Hydroxide | 0.1 g |
| Disodium EDTA | 0.1 g |
| Squalane | 0.1 g |
| Phenoxyethanol | 0.1 g |
| Methylparaben | 0.2 g |
| Perfume | 0.3 g |
| Water | to 100 g |

Example 10 (Leave-on Treatment without Lipids, Fatty Acid and Dicarboxylic Acid)

| Raw Material | Amount |
| --- | --- |
| Propylenglycol | 3.0 g |
| Amodimethicone | 1.3 g |
| Quaternium-80 | 1.0 g |
| Cetrimonium Chloride | 1.0 g |
| Behentrimonium Chloride | 1.6 g |
| Amodimethicone | 0.3 g |
| D,L-Tocopheryl Acetate | 0.2 g |
| Polyquaternium-37 | 0.125 g |
| Sodium Hydroxide | 0.1 g |
| Disodium EDTA | 0.1 g |
| Phenoxyethanol | 0.1 g |
| Methylparaben | 0.2 g |
| Perfume | 0.3 g |
| Water | to 100 g |

Example 11 (Composition for Mixing with a Bleaching Agent, a Coloring Agent, or a Permanent Hair Waving Agent)

| Raw Material | Amount |
| --- | --- |
| Malic Acid | 9.0 g |
| Quaternium-80 | 2.25 g |
| Cetrimonium Chloride | 1.9 g |
| Sodium Hydroxide | 2.9 g |
| Sodium Sulfite | 0.25 g |
| Coceth-10 | 0.9 g |
| Propylene Glycol | 0.75 g |
| Butylene Glycol | 0.5 g |
| Phenoxyethanol | 0.9 g |
| PEG-35 Castor Oil | 0.3 g |
| Glyceryl Monooleate | 0.25 g |
| Oleic Acid | 0.1 g |
| Squalane | 0.1 g |
| Water | to 100 g |

STATEMENTS OF EMBODIMENTS OF THE INVENTION

The following statements of embodiments of the invention describe aspects, features and parameters of the methods, compositions, and treatments according to the invention. These statements provide further disclosure of these aspects, features and parameters and may serve as claims of the invention.

1. A hair treatment composition comprising:
   a) a C3-C13 linear or branched saturated or unsaturated dicarboxylic acid, the saturated dicarboxylic acid being optionally substituted with one hydroxyl group, and the dicarboxylic acid being at a weight percentage concentration of from about 0.05 wt % to about 15 wt %;
   b) a C10-C30 saturated or unsaturated fatty monocarboxylic acid at a weight percentage concentration of about 0.01 wt % to about 10 wt %;
   c) a C10-C40 saturated or unsaturated linear or branched hydrocarbon at a weight percentage concentration of about 0.01 wt % to about 1 wt %;
   d) a fatty acid ester of the C10-C30 saturated or unsaturated monocarboxylic acid and a C3-C6 mono-ol, diol or triol esterifying alcohol, the fatty acid ester being at a weight percentage concentration of about 0.1 wt % to about 10 wt %;
   e) a cosmetically acceptable aqueous or aqueous-organic medium; and
   wherein each of the dicarboxylic acid and/or the fatty monocarboxylic acid independently comprises the free acid or the cosmetically acceptably salt thereof and all weight percentages are relative to the total weight of the composition.

2. A hair treatment composition according to statement 1 wherein the linear or branched saturated or unsaturated C3-C13 dicarboxylic acid with an optional hydroxyl group comprises:
   a) a C3-C13 linear saturated dicarboxylic acid, preferably a C3-C6 dicarboxylic acid;
   b) a C3-C13 linear saturated dicarboxylic acid with one hydroxyl group, preferably a C3-C6 linear saturated dicarboxylic acid with one hydroxyl group;
   c) a C4-C13 linear unsaturated dicarboxylic acid with one olefinic unsaturation in the carbon chain of the dicarboxylic acid, preferably a C4-C6 linear unsaturated dicarboxylic acid;
   d) a C5-C13 branched unsaturated dicarboxylic acid with one olefinic unsaturation as the branch group, preferably a C5-C6 branched unsaturated dicarboxylic acid with the branch being the olefinic group;
   e) and any combination thereof.

3. A hair treatment composition according to any of the preceding statements wherein the dicarboxylic acid is selected from the group consisting essentially of malonic acid, succinic acid, glutaric acid, adipic acid, brassylic acid, malic acid, hydroxysuccinic acid, hydroxyglutaric acid, fumaric acid, maleic acid, itaconic acid, glutaconic acid, salts thereof, and any combination thereof.

4. A hair treatment composition according to any of the preceding statements wherein the C10-C30 saturated or unsaturated fatty monocarboxylic acid is a C16-C22 saturated fatty monocarboxylic acid or a C16-C22 unsaturated monocarboxylic acid with one olefinic group.

5. A hair treatment composition according to any of the preceding statements wherein the esterifying alcohol of the fatty acid ester is a C3-C6 triol, preferably a C3 triol.

6. A hair treatment composition according to any of the preceding statements wherein the saturated or unsaturated linear or branched hydrocarbon is a C26-C40 hydrocarbon, preferably a C28-C30 hydrocarbon, more preferably squalane or squalene.

7. A hair treatment composition according to any of the preceding statements wherein the dicarboxylic acid is malic acid or hydroxyglutaric acid, preferably malic acid, the fatty monocarboxylic acid is oleic acid or palmitoleic acid, preferably oleic acid, the hydrocarbon is squalane or squalene, preferably squalane, and the fatty acid ester is glyceryl monooleate or glyceryl mono-palmitoleate, preferably glyceryl monooleate.

8. A hair treatment composition according to any of the preceding statements further comprising at least one of a cationic surfactant, a silicone conditioner, an anionic surfactant, a bleaching agent, a coloring agent, and a permanent hair waving agent.

9. A hair treatment composition according to any of the preceding statements wherein the concentration of the dicarboxylic acid comprises a range of from about 0.1 wt % to about 10 wt % and the concentration of the fatty monocarboxylic acid comprises a range of about 0.015 wt % to about 1 wt %.

10. A hair treatment composition according to any of the preceding statements wherein the sum of the concentrations of any the fatty acid ester and hydrocarbon present in the hair treatment composition comprises a range of about 0.01 wt % to about 10 wt %.

11. A hair treatment composition according to any of the preceding statements wherein the weight percentage ratio of dicarboxylic acid to fatty monocarboxylic acid comprises about 2:1 to about 10:1, preferably about 2:1 to about 5:1.

12. A hair treatment composition according to any of the preceding statements wherein the medium comprises an aqueous organic medium optionally with a C2-C6 monoalcohol.

13. A method for treating anagenic hair comprising applying to the anagenic hair a hair treatment composition of any of the preceding statements.

14. A method according to statement 13 wherein the hair treatment composition is diluted with water before or while applying to the hair or alternatively is applied to the hair without dilution with water or other medium.

15. A hair treatment composition according to any of the preceding statements wherein the hair treatment composition comprises at least a part of a hair conditioner, hair cream, hair shampoo, dry shampoo, hair rinse, hair liquid, hair oil, hair pomade, hair foam, hair spray, hair tonic and/or hair lotion.

MISCELLANEOUS STATEMENTS

The invention has been described broadly and generically herein. Each of the narrower species and subgeneric groupings falling within the generic disclosure also form part of the invention. This includes the generic description of the invention with a proviso or negative limitation removing any matter from the genus, regardless of whether or not the excised material is specifically recited herein. The inventions, examples, results and statement of embodiments described, stated and claimed herein may have attributes and embodiments include, but not limited to, those set forth or described or referenced in this application.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed and as provided by the statements of embodiments. Thus, it will be understood that although the present invention has been specifically disclosed by various nonlimiting embodiments and/or preferred nonlimiting embodiments and optional features, any and all modifications and variations of the concepts herein disclosed that may be resorted to by those skilled in the art are considered to be within the scope of this invention as defined by the appended claims and the statements of embodiments.

All patents, publications, scientific articles, web sites and other documents and ministerial references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such patent, publication, scientific article, web site, electronically available information, textbook or other referenced material or document.

The written description of this patent application includes all claims, examples and statements of embodiments. All claims and statements of embodiments including all original claims are hereby incorporated by reference in their entirety into the written description portion of the specification and the right is reserved to physically incorporate into the written description or any other portion of the application any and all such claims and statements of embodiments. Thus, for example, under no circumstances may the patent be interpreted as allegedly not providing a written description for a claim on the assertion that the precise wording of the claim is not set forth in haec verba in written description portion of the patent.

While the invention has been described in conjunction with the detailed description thereof, the foregoing description is intended to illustrate and not limit the scope of the invention, which is defined by the scope of the appended claims and the statements of embodiments. Thus, from the foregoing, it will be appreciated that, although specific nonlimiting embodiments of the invention have been described herein for the purpose of illustration, various modifications may be made without deviating from the scope of the invention. Other aspects, advantages, and modifications are within the scope of the following claims and the present invention is not limited except as by the appended claims and the statements of embodiments.

The specific methods and compositions described herein are representative of preferred nonlimiting embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in nonlimiting embodiments or examples of the present invention, the terms "comprising", "including", "containing", "providing" and the like are to be read expansively and without limitation.

The methods and processes illustratively described herein suitably may be practiced in differing orders of steps, and that they are not necessarily restricted to the orders of steps indicated herein or in the claims.

What is claimed is:

1. A hair treatment composition comprising:
   a stand-alone hair conditioner, or a stand-alone rinse-off conditioner, or a stand-alone leave-on conditioner, or a stand-alone mask of at least components a-f wherein:
   a) component a is a C3-C13 linear saturated dicarboxylic acid substituted with one hydroxyl group wherein the dicarboxylic acid is present at a weight percentage concentration of from about 0.05 wt % to about 15 wt %;
   b) component b is a C10-C30 mono-unsaturated fatty monocarboxylic acid at a weight percentage concentration of about 0.01 wt % to about 10 wt %;
   c) component c is a C10-C40 saturated or unsaturated linear or branched hydrocarbon at a weight percentage concentration of about 0.01 wt % to about 1 wt %;
   d) component d is a fatty acid mono-ester of the C10-C30 mono-unsaturated monocarboxylic acid and a C3-C6 triol esterifying alcohol, the fatty acid mono-ester being at a weight percentage concentration of about 0.1 wt % to about 10 wt %;
   e) component e is a cosmetically acceptable aqueous or aqueous-organic medium at a weight percentage concentration of from about 20 wt % to about 95 wt % relative to the total weight of the hair treatment composition and the aqueous-organic medium comprises from about 50 wt % to about 99 wt % water relative to the total weight of the medium;
   f) component f is one or more cationic surfactants;
   wherein each of the dicarboxylic acid and the fatty monocarboxylic acid in the stand-alone hair conditioner or stand-alone leave-on conditioner or stand-alone rinse-off conditioner or stand-alone mask independently consists of the free acid or a cosmetically acceptable alkali metal or alkali earth metal salt thereof; and
   wherein a weight percentage ratio of dicarboxylic acid to fatty monocarboxylic acid comprises about 2:1 to about 10:1; and
   wherein all weight percentages are relative to the total weight of the hair treatment composition except as otherwise recited; and,
   wherein the pH of the hair treatment composition is from about 6 to about 8; and,
   wherein the stand-alone hair conditioner, or stand-alone rinse-off conditioner, or stand-alone leave-on conditioner, or stand-alone mask is not a shampoo containing an anionic surfactant alone or in combination with a nonionic surfactant.

2. The hair treatment composition according to claim 1 wherein the dicarboxylic acid comprises one of malic acid, hydroxysuccinic acid, hydroxyglutaric acid, the salts thereof, or any combination thereof.

3. The hair treatment composition according to claim 1 wherein the C10-C30 mono-unsaturated fatty monocarboxylic acid comprises a C16-C22 unsaturated monocarboxylic acid with one olefinic group.

4. The hair treatment composition according to claim 1 wherein the triol esterifying alcohol is a C3 triol.

5. The hair treatment composition according to claim 1 wherein the saturated or unsaturated linear or branched hydrocarbon comprises a C26-C40 hydrocarbon.

6. The hair treatment composition according to claim 5 comprising a C28-C30 hydrocarbon.

7. The hair treatment composition according to claim 6 comprising squalene or squalane.

8. The hair treatment composition according to claim 1 wherein the dicarboxylic acid is malic acid or hydroxyglutaric acid, the fatty monocarboxylic acid is oleic acid or palmitoleic acid, the hydrocarbon is squalane or squalene, and the fatty acid ester is glyceryl monooleate or glyceryl mono-palmitoleate.

9. The hair treatment composition according to claim 8 comprising malic acid, oleic acid, squalane and glyceryl monooleate.

10. The hair treatment composition according to claim 1 further comprising a conditioning additive of at least one of one or more of each of a linear or branched, saturated or unsaturated fatty C12-C30 alcohol, a polyethylene glycol (PEG'S), a cationic polymer, an anti-oxidant, a preservative, a UV protectant, a viscosity control agent, a humectant, an emollient, an emulsifier other than an anionic surfactant, a silica, a hair strand thickener, a pH adjuster, a buffering agent, a chelating agent, a bleaching agent, a permanent hair waving agent, an anti-dandruff, an anti-fungal, an anti-microbial, anti-itch, vitamin E, vitamin F, salicylic acid, phenoxyethanol, ethylhexyl glycerin, a glycol, glycolic acid, PCA, erythritol, glycerin, a lactate, a hyaluronate, allantoin, a betaine, sorbitol, a glutamate, a xylitol, menthol, menthyl lactate, isocyclomone, benzyl alcohol, a fragrance, a pigment, a colorant, an essential oil, a shine agent, a natural extract, a sensate, an antifoaming agent, a dimethicone, a dimethiconol, a cyclic silicone, a silicone modified with amine groups or quaternary ammonium groups, and any combination thereof.

11. The hair treatment composition according to claim 1 wherein the concentration of the dicarboxylic acid comprises a range of from about 0.1 wt % to about 10 wt % and the concentration of the fatty monocarboxylic acid comprises a range of about 0.015 wt % to about 1 wt %.

12. The hair treatment composition according to claim 1 wherein the weight percentage ratio of dicarboxylic acid to fatty monocarboxylic acid comprises about 2:1 to about 5:1.

13. The hair treatment composition according to claim 1 wherein the medium comprises an aqueous or aqueous organic medium wherein the aqueous organic medium comprises a C2-C6 monoalcohol; and the weight percentage range of the medium relative to the total weight if the composition comprises from about 60 wt % to about 95 wt %.

14. The hair treatment composition according to claim 1 wherein the one or more cationic surfactants is one or more C14-C30 linear alkyl amines quaternized with three methyl groups.

15. The hair treatment composition according to claim 10 wherein the conditioner additive is one or more linear or branched, saturated or unsaturated fatty C12-C30 alcohols, or one or more cationic polymers, or one or more emulsifiers other than an anionic surfactant, or one or more pH adjuster, or one or more chelating agents, or phenoxyethanol, or ethylhexyl glycerin, or one or more fragrances, or one or more essential oils, or one or more natural extracts, or one or more preservatives, or vitamin E, or any combination thereof.

16. A hair treatment composition consisting of:
a stand-alone hair conditioner, or a stand-alone rinse-off conditioner, or a stand-alone leave-on conditioner, or a stand-alone mask of components a-g wherein:
a) component a is a C3-C13 linear saturated dicarboxylic acid substituted with one hydroxyl group wherein the dicarboxylic acid is present at a weight percentage concentration of from about 0.05 wt % to about 15 wt %;
b) component b is a C10-C30 mono-unsaturated fatty monocarboxylic acid at a weight percentage concentration of about 0.01 wt % to about 10 wt %;
c) component c is a C10-C40 saturated or unsaturated linear or branched hydrocarbon at a weight percentage concentration of about 0.01 wt % to about 1 wt %;
d) component d is a fatty acid mono-ester of the C10-C30 mono-unsaturated monocarboxylic acid and a C3-C6 triol esterifying alcohol, the fatty acid mono-ester being at a weight percentage concentration of about 0.1 wt % to about 10 wt %;
e) component e is a cosmetically acceptable aqueous or aqueous-organic medium at a weight percentage concentration of from about 20 wt % to about 95 wt % relative to the total weight of the hair treatment composition and the aqueous-organic medium comprises from about 50 wt % to about 99 wt % water relative to the total weight of the medium;
f) component f is one or more cationic surfactants selected from the group consisting of one or more C14-C30 linear alkyl amines quaternized with three methyl groups;
g) component g is one or more optional additives and is selected from the group consisting of a linear or branched, saturated or unsaturated fatty C12-C30 alcohol, a polyethylene glycol a cationic polymer, a preservative, a UV protectant, a viscosity control agent, a humectant, an emollient, an emulsifier other than an anionic surfactant, a hair strand thickener, a pH adjuster, a chelating agent, an anti-dandruff, an anti-fungal, an anti-microbial, an anti-itch vitamin E, phenoxyethanol, ethylhexyl glycerin, a fragrance, a pigment, a colorant, an essential oil, a natural extract, and any combination thereof;
wherein each of the dicarboxylic acid and the fatty monocarboxylic acid in the stand-alone hair conditioner or stand-alone leave-on conditioner or stand-alone rinse-off conditioner or stand-alone mask independently consists of the free acid or a cosmetically acceptable alkali metal or alkali earth metal salt thereof; and
wherein a weight percentage ratio of dicarboxylic acid to fatty monocarboxylic acid comprises about 2:1 to about 10:1; and,
wherein all weight percentages are relative to the total weight of the hair treatment composition except as otherwise recited.

17. The hair treatment composition according to claim 16 wherein the optional component g is selected from the group consisting of one or more linear or branched, saturated or unsaturated fatty C12-C30 alcohols, one or more cationic polymers, one or more emulsifiers other than an anionic surfactant, one or more pH adjusters, one or more chelating agents, phenoxyethanol, ethylhexyl glycerin, one or more fragrances, one or more essential oils, one or more natural extracts, one or more preservatives, vitamin E and any combination thereof.

18. The hair treatment composition according to claim 16 wherein the dicarboxylic acid is malic acid or hydroxyglutaric acid, the fatty monocarboxylic acid is oleic acid or palmitoleic acid, the hydrocarbon is squalane or squalene, and the fatty acid ester is glyceryl monooleate or glyceryl mono-palmitoleate.

19. The hair treatment composition according to claim 18 comprising malic acid, oleic acid, squalane and glyceryl monooleate.

20. A method for treating anagenic hair comprising applying to the anagenic hair a hair treatment composition of claim 1.

21. A method according to claim 10 wherein the hair treatment composition is diluted with water before or while applying to the hair or alternatively is applied to the hair without dilution with water or other medium.

\* \* \* \* \*